United States Patent [19]

Spector

[11] Patent Number: 4,648,272

[45] Date of Patent: Mar. 10, 1987

[54] STRENGTH/WEIGHT MEASURING SCALE

[76] Inventor: Donald Spector, 380 Mountain Rd., Union City, N.J. 07087

[21] Appl. No.: 799,600

[22] Filed: Nov. 19, 1985

[51] Int. Cl.$^4$ .......................... A61B 5/22; G01G 19/50
[52] U.S. Cl. ......................................... 73/380; 177/245
[58] Field of Search .......................... 73/379, 380, 381; 177/245

[56] References Cited

U.S. PATENT DOCUMENTS

| | | | |
|---|---|---|---|
| 712,072 | 10/1902 | Jordan | 73/381 |
| 750,819 | 2/1904 | Cummings | 73/381 X |
| 4,113,039 | 9/1978 | Ozaki et al. | 177/25 |
| 4,301,879 | 11/1981 | Dubow | 177/5 |

Primary Examiner—Charles A. Ruehl
Attorney, Agent, or Firm—Michael Ebert

[57] ABSTRACT

A scale selectively operative in a weighing mode to measure body weight and in a strength mode to measure muscular strength. The scale includes a base which rests on the ground, above which is a depressible platform to compress a spring interposed between the platform and the base. The degree to which the spring is compressed, either by the platform or by the base, is converted into an analog or digital readout. Anchored on the base and extending through an opening in the platform is an upright post terminating in a handle that is elevated relative to the platform. Also provided is an adjustable stop which is coupled to the platform. When actuated, the stop engages the ground to prevent depression of the platform. In the weighing mode, the stop is disabled, and when an individual steps on the platform, the resultant readout indicates his body weight. In the strength mode, the stop is actuated, and when the individual steps on the platform and then exerts an upward force on the handle in accordance with his strength, the resultant readout is indicative of strength and is independent of body weight.

7 Claims, 3 Drawing Figures

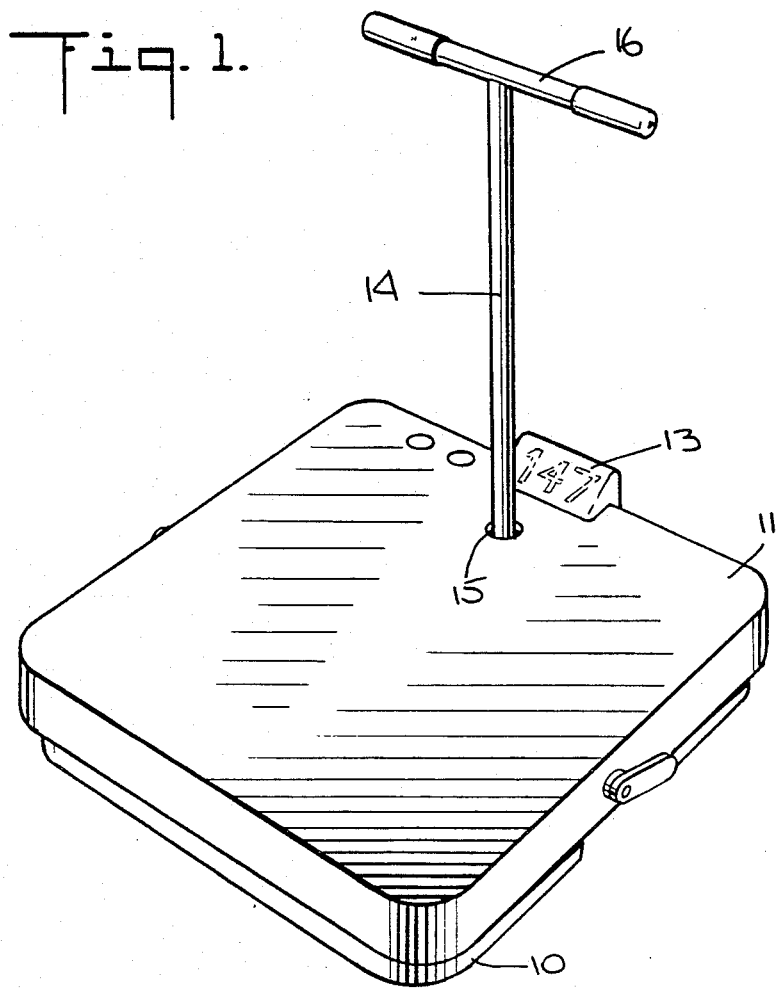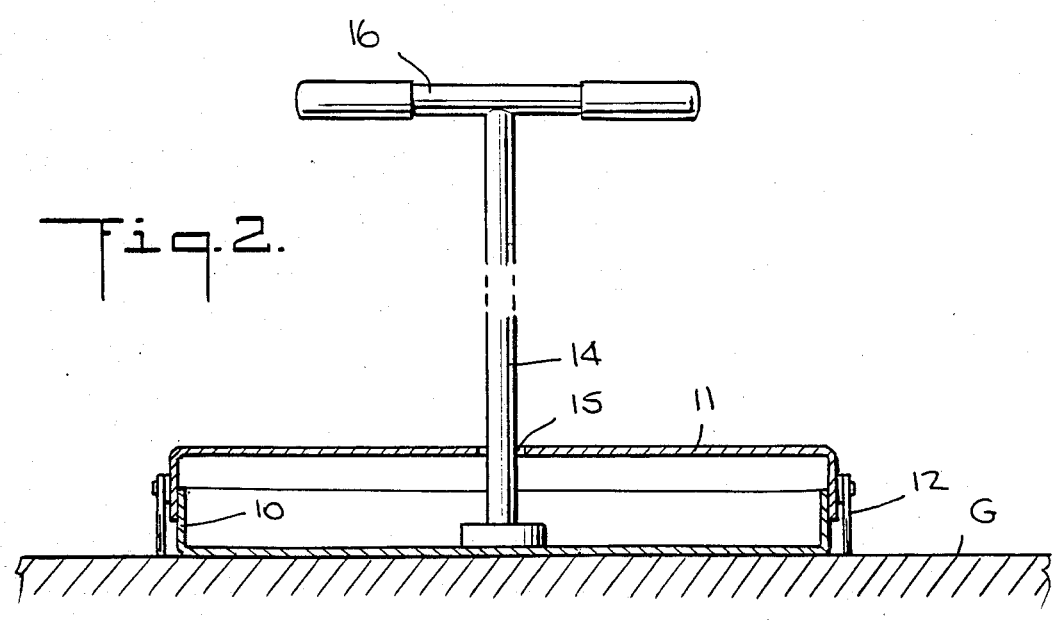

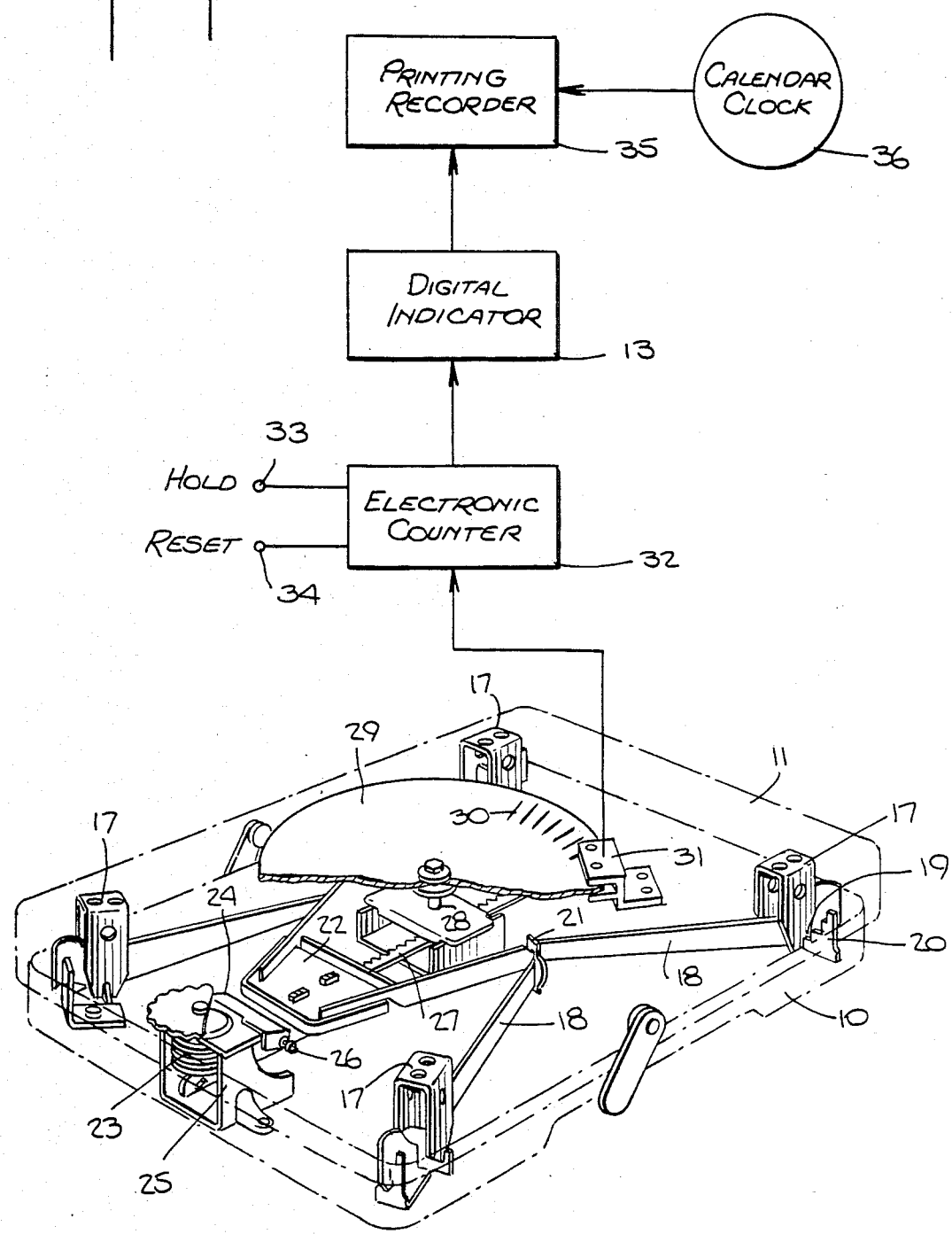

STRENGTH/WEIGHT MEASURING SCALE

BACKGROUND OF INVENTION

1. Field of Invention

This invention relates generally to scales which provide a reading of body weight, and more particularly to a scale of this type which is selectively operable to provide a reading of muscular strength independent of body weight.

2. Status of Prior Art

Exercise and body development for maintaining fitness and in assisting in physical growth can be practiced at home. Thus, tension-resisting devices of various types are commonly used for the development of back, shoulder and arm muscles.

When undergoing a program of exercise, it is desirable to keep tabs on the effect thereof on the body weight of the exerciser. Thus, if one undertakes an exercise program with a view not only to gaining muscular strength but also toward reducing body weight, the increase in strength may be accompanied by a gain rather than a loss in weight. In some instances one seeks to increase body weight when following a program of muscular development. Hence, the correlation of changing strength to weight is of concern to the serious exerciser.

The use of a home or bathroom scale to measure body weight is commonplace. But the measurement of strength normally requires a separate scale. Thus, the patent to Newman, U.S. Pat. No. 2,784,592, discloses a muscle tester having a handle which is grasped by the user and pushed, the resultant force being indicated on a gauge.

To make it possible to use a conventional bathroom weighing scale as a hand grip testing device, Richard et al., in U.S. Pat. No. 3,848,468, provides a grip accessory that is attachable to a body weighing scale. This accessory includes a plunger which when pressed downwardly by a gripping action causes the dial of the scale to indicate the strength of the grip. In order to use the scale to measure body weight, the accessory must be detached therefrom and the scale placed on the ground.

Bradley et al., in U.S. Pat. No. 3,785,644, also uses a weighing scale to measure strength, and for this purpose an overhead bar is tied by ropes to the ground. The user, when raising the bar, stands on the weighing scale between the ropes. In this arrangement, in order to measure strength, after the individual steps on the scale it must then be zero set, so that regardless of the user's weight, the scale reads zero until he lifts the bar and imposes a force on the spring-operated scale that causes it to read above zero.

Hence, should the user, after measuring his strength, now wish to measure his weight, the scale must be reset so that it reads zero in the absence of body weight. This requirement represents a practical drawback, particularly since as the user changes weight in the course of an exercise program, it becomes necessary to provide a different zero setting each time the scale is used to measure strength.

SUMMARY OF INVENTION

In view of the foregoing, the main object of this invention is to provide a strength/weight measuring scale which makes use of a conventional body weighing scale that need not be re-zeroed each time a reading of body weight or muscular strength is taken.

More particularly, an object of this invention is to provide a selective scale of the above type in which the user steps on the scale to either measure weight or muscular strength, the user when measuring muscular strength grasping a handle to exert a force of the scale.

Also, an object of the invention is to provide a dual-purpose scale of the above type which requires only a relatively minor and inexpensive modification of an existing bathroom scale, so that a scale of this type can be manufactured and sold at relatively low cost.

Briefly stated, these objects are attained in a scale selectively operative in a weighing mode to measure body weight or in a strength mode to measure muscular strength. The scale includes a base which rests on the ground, above which is a depressible platform to compress a spring interposed between the platform and the base. The degree to which the spring is compressed, either by the platform or by the base, is converted into an analog or digital readout.

Anchored on the base and extending through an opening in the platform is an upright post terminating in a handle that is elevated relative to the platform. Also provided is an adjustable stop which is coupled to the platform. When actuated, the stop engages the ground to prevent depression of the platform. In the weighing mode, the stop is disabled, and when an individual steps on the platform, the resultant readout indicates his body weight. In the strength mode, the stop is actuated, and when the individual steps on the platform and then exerts an upward force on the handle in accordance with his strength, the resultant readout is indicative of strength and is independent of body weight.

OUTLINE OF DRAWINGS

For a better understanding of the invention as well as other objects and further features thereof, reference is made to the following detailed description to be read in conjunction with the accompanying drawings, wherein:

FIG. 1 is a perspective view of a strength/weight measuring scale in accordance with the invention;

FIG. 2 is a section taken through the scale, the spring works being omitted; and FIG. 3 shows the internal mechanism of the scale.

DESCRIPTION OF INVENTION

Scale Structure

Referring now to FIGS. 1 and 2, there is shown a scale in accordance with the invention constituted by a base 10 which rests on the ground G, and a depressible platform 11 thereabove provided on either side with pivoted stops 12, which are adjustable. The stops, when retracted, are disabled and permit the platform to be depressed by a person standing thereon, and when rendered operative by swinging the stops downwardly to engage ground G, the platform is held at its normally raised position above the base.

The scale is provided with a digital readout 13 mounted at the back end of the platform so that it is readable by one who stands on the platform. Also provided is an upright post 14 that is anchored in base 10 at a center position adjacent the back end thereof. Post 14 extends upwardly through an opening 15 in the platform and terminates in a handle 16 which is elevated above the platform to a convenient height. In practice, the readout may be mounted on the handle at its junction with the post.

As shown in FIG. 3 which exposes the internal mechanism of the scale, platform 11 is supported by four corner pieces 17 carried on levers 18. Though intermediate edges 19, one end of each lever is pivotally supported on a corner bracket 20 mounted on base 10. Levers 18 are coupled by rings 21 to a hanger 22, the action of the levers being applied by the hanger to a main spring 23. The compression of the main spring is transmitted to a link lever 24 pivotally supported on a frame 25 within which the lever is seated, this transmission being effected through link pins 26, the link lever 24 acting to translate a toothed rack 27. This scale arrangement is similar to that disclosed in U.S. Pat. No. 4,113,039.

As rack 27 is translated, this acts through a pinion (not shown) to rotate the shaft 28 of a graduated sector plate 29 to an extent determined by the degree of spring compression. Graduated plate 29 is provided with a series of indicia 30 in slit form, so that if the plate were exposed to view and rotated relative to a fixed pointer, it would provide an analog readout for the scale.

However, to provide a digital readout, associated with scale plate 27 is a photodetector station 31. This includes a light source that projects a light beam through the slit aligned therewith, this beam being intercepted by a photodiode to generate a pulse each time a slit on the rotating scale plate is aligned with the photodetector station. Thus, when the scale operates, if the scale plate is caused to rotate to an extent causing 128 slits to traverse the photodetector station, then 128 pulses will be transmitted to a resettable electronic counter 32. The total count of counter 32 is applied to digital readout 13 to provide a reading of 128 pounds.

In practice, counter 32 may be provided with a hold button 33 to retain the count accumulated therein so that the reading is held for the convenience of the user, and a reset button 34 to reset the counter to zero preparatory to a subsequent reading. These buttons may be mounted on the platform so that the can can be actuated by the foot of the user.

Scale Operation

When the scale is to be used in the weighing mode, stops 12 are disabled so that the platform is free to depress; hence when the user then steps on the scale, the depressed platform compresses the main spring to provide a reading of body weight in the fashion of a conventional bathroom scale.

When the same scale is to be used to measure the strength of the user, the user first actuates the stops 12 so as to prevent depression of the platform. He then steps on the platform and grasps handle 16 and pulls on it to exert a force that depends on his strength. This action causes displacement of base 10 relative to the then fixed platform 12 to compress the main spring 23. The resultant readout on digital indicator 13 then represents the strength of the user and is independent of body weight. In other words, if the strength readout is, say, 150 lbs., that is equivalent to the user lifting a 150 lb. weight.

In order to provide a progress report in which the body weight of the exerciser is correlated with his changing weight, the output of digital indicator 13 may be fed to a printing recorder 35 which cooperates with a calendar clock 36, thus when the recorder is rendered operative, it will then record and print out the body weight reading and the strength reading, each reading being printed against a time, day and date indication. In this way, the user will have a running record of his progress in the course of an exercise program.

Where there has been shown a spring-type mechanical weighing scale, in practice the invention may be realized in an electronic scale using an electromagnetic, a capacitive, or a piezoelectric transducer to convert the displacement of the platform relative to the base to a weight or strength reading.

I claim:

1. A scale selectively operative in a weighing mode to measure body weight, and in a strength mode to measure muscular strength, the scale comprising:
    A a base restable on the ground;
    B a depressible platform supported above the base;
    C a transducer interposed between the platform and the base to provide a signal indicative of the extent to which the platform in displaced relative to the base or vice versa;
    D a converter coupled to the transducer to provide a readout;
    E an upright post mounted on the base and extending through an opening in the platform, said post terminating in a handle which is elevated above the platform and can be grasped by one standing thereon; and
    F selective means to prevent depression of the platform, whereby when these means are disabled in the weighing mode and the platform is depressed by a user standing thereon, the reading is that of body weight, and when these means are rendered operative in the strength mode, then one standing on the platform and pulling up on the handle to exert an upward force on the base, the reading will then be of strength and be independent of body weight.

2. A scale as set forth in claim 1, whereas said transducer is a compressible spring, and said converter translates the degree to which the spring is compressed to a scalar reading.

3. A scale as set forth in claim 1, wherein said selective means is constituted by at least one adjustable stop pivoted on the platform and adapted, when actuated, to engage the ground.

4. A scale as set forth in claim 1, wherein said converter includes means to provide a digital readout.

5. A scale as set forth in claim 4, wherein said converter produces signal pulses whose number depends on the relative movement of the platform and base, and a counter responsive to said pulses whose total count is applied to a digital indicator.

6. A scale as set forth in claim 5 further including a recording printer associated with the counter.

7. A scale as set forth in claim 6 including a calendar clock associated with the printer.

* * * * *